United States Patent [19]
Sheridan

[11] Patent Number: 5,083,621
[45] Date of Patent: Jan. 28, 1992

[54] CONTINUOUSLY ENGAGED TANGENTIAL DRIVING TOOL

[75] Inventor: Thomas L. Sheridan, Monte Sereno, Calif.

[73] Assignee: Orthopedic Systems, Inc., Hayward, Calif.

[21] Appl. No.: 542,159

[22] Filed: Jun. 22, 1990

Related U.S. Application Data

[63] Continuation-in-part of Ser. No. 297,762, Nov. 17, 1989.

[51] Int. Cl.⁵ .............................................. B25B 13/46
[52] U.S. Cl. ..................................... 173/164; 173/163; 81/57.46
[58] Field of Search ................. 173/163, 164, 12; 81/57.46, 163, 60; 254/100; 606/61, 53

[56] References Cited

U.S. PATENT DOCUMENTS

| | | | |
|---|---|---|---|
| 2,466,456 | 4/1949 | Lybyer | 81/57 |
| 2,817,257 | 12/1957 | Kniser | 81/58.1 |
| 3,023,652 | 3/1962 | Feldman | 81/60 |
| 4,027,558 | 6/1977 | Fish | 81/52.4 R |
| 4,279,314 | 7/1981 | Taub | 173/163 |
| 4,436,004 | 3/1984 | Chang | 81/60 |

Primary Examiner—Mark Rosenbaum
Assistant Examiner—Allan M. Schrock
Attorney, Agent, or Firm—Flehr, Hohbach, Test, Albritton & Herbert

[57] ABSTRACT

Wrench for continuous driving engagement with a rotatively driven element such as a screw, bolt or nut, which is particularly suitable for use where the ends of the driven element are not accessible and in applications where space for manipulation of the tool is limited such as in spinal fusion surgery. The wrench has a peripheral driving element which can be engaged from the side with the driven element, and an articulating handle which enables the wrench to rotate the driven element through a substantial angle with only a few degrees of handle movement.

10 Claims, 3 Drawing Sheets

CONTINUOUSLY ENGAGED TANGENTIAL DRIVING TOOL

CROSS-REFERENCE TO RELATED APPLICATION

This is a continuation-in-part of Ser. No. 297,762, filed Jan. 17, 1989.

BACKGROUND

1. Field of Invention

This invention pertains generally to wrenches and other tools and, more particularly, to apparatus for applying a driving torque to a driven element.

2. Description of Prior Art

It is common practice to use rotatively driven mechanical devices to draw two objects together or to push two objects apart. Common examples of devices for drawing objects together are bolts and nuts, and an example of a device for pushing objects apart is a jack screw. Such devices commonly have some feature that makes it possible to rotate them with a tool. A nut or the head of a bolt, for example, might have a hexagonal shape, a square shape, or another shape suitable for engagement by a wrench, and the head of a bolt or screw may be provided with a slot or other suitable opening for engagement by a screwdriver.

It is frequently desirable to be able to engage these devices with a tool to provide continuous rotation of the device without having to disengage and re-engage the tool for each successive increment of rotation. This continuous turning capability is particularly useful in situations where time is critical or space is limited.

Heretofore, some tools have been provided for continuous mating engagement with bolts, nuts and the like to apply a driving torque to them. Common examples of such tools include socket wrenches with ratcheting handles and certain box wrenches with ratcheting mechanisms. However, the tools heretofore provided of this type have one common drawback that severely limits their use. They require that the end of the nut, bolt or other driven device be unobstructed and accessible because the tool must be placed on or over the end of the device to apply the torquing force.

Many times the ends of the driven devices are covered, obstructed or otherwise not accessible, in which case continuously engaged torquing tools cannot be used, and some other tool such as an open end wrench or a pair of pliers must be employed. These other tools do not allow continuous turning of the driven device, but instead require that the tool be disengaged and re-engaged for successive increments of rotation. The process of repeatedly repositioning the tool and making only a limited degree of rotation with each positioning is inefficient and time consuming. It is especially undesirable and difficult when working in small, confined spaces like those that often occur when performing surgical procedures.

One surgical procedure where space for manipulation of a wrench is limited is back fusion surgery. In back fusion surgery, a spinal bone separating device is often used to separate the spinal bones in preparation for the bone fusion. Such a bone separation device consists of two threaded hooks that engage the bones to be separated. These hooks mount on oppositely threaded sections of a jack screw which is rotated by means of a hex shaped nut affixed to the screw between the oppositely threaded sections. Access to the nut from the ends of the screw is blocked by the hooks so that a continuously engaged torquing tool such as a socket wrench cannot be utilized to turn the screw. An open ended box wrench is the tool which is currently used in this situation. With this tool, the limited space available and the limited visibility in such surgery, the task of separating the bones is extremely difficult and time consuming for doctors to perform.

OBJECTS AND SUMMARY OF THE INVENTION

It is in general an object of the invention to provide a new and improved tool for continuous driving engagement with a rotatively driven element such as a screw, bolt or nut.

Another object of the invention is to provide a tool of the above character which overcomes the limitations and disadvantages of tools heretofore provided.

Another object of the invention is to provide a tool of the above character which can be utilized in situations where the ends of the driven element are not accessible and/or space for manipulation of the tool is limited.

Another object of the invention is to provide a tool of the above character which is particularly suitable for use in spinal fusion surgery.

These and other objects are achieved in accordance with the invention by providing a wrench having a peripheral driving element adapted to be engaged from the side with a driven element, a relatively short head which carries the driving element and is adapted to impart a driving torque to the driving element when swung back and forth about the axis of the driven element, means for holding the driving element in peripheral driving engagement with the driven element, an elongated handle for swinging the head back and forth about the axis of the driven element, and means pivotally connecting the elongated handle to the relatively short head for movement about an axis parallel to the axis of the driven element to permit articulation between the handle and the head as the head is swung back and forth to produce the tangential driving force.

BRIEF DESCRIPTION OF THE DRAWINGS

In FIG. 1, a rotational driving tool or wrench 16 is shown in driving engagement with a bone separator 17.

Figure 1:
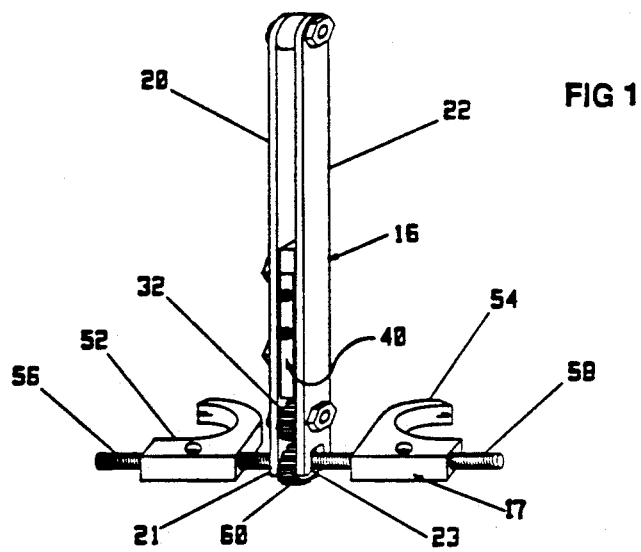
FIG. 1 is an isometric view of one embodiment of a continuously engaged torquing tool according to the invention in driving engagement with a bone separator of the type employed in spinal fusion surgery.
Figure 2:
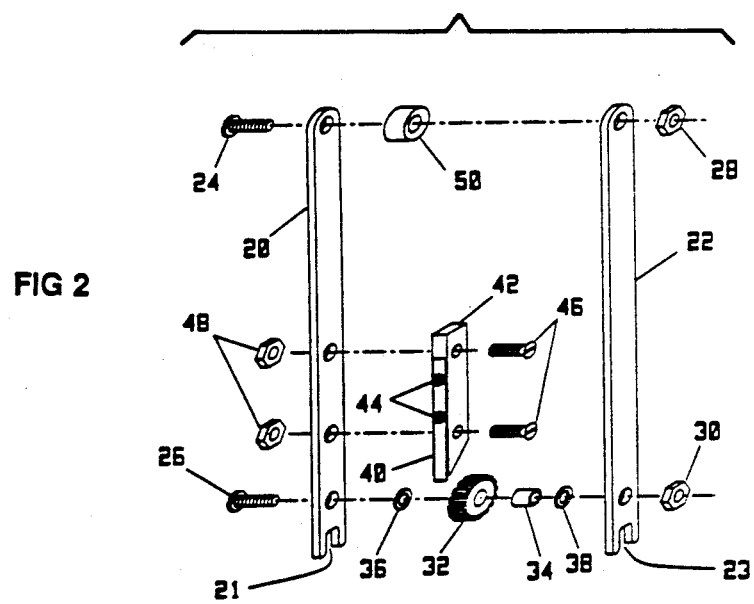
FIG. 2 is an exploded view of the torquing tool in the embodiment of FIG. 1.

The tool has a pair of side plates or cover plates 20, 22, typically 5 inches in length, which are secured together in spaced parallel relation by screws 24, 26 and nuts 28, 30 and form a handle by which the tool can be manipulated. A torquing drive gear 32, typically a 0.5 inch diameter by 0.16 inch thick spur gear with 18 teeth, is rotatively mounted on screw 26, with a bushing 34 between the gear and the screw, and spacers 36, 38 between the bushing and the side plates. A flat spring 40, typically made of spring steel, is attached to a mounting block 42 by screws 44, and the mounting block is attached to side plate 20 by screws 46 and nuts 48. One end of the flat spring projects about 0.1 inch from the mounting block and engages the teeth of drive gear 32 to serve as a pawl which permits the gear to rotate in one direction only. A spacer 50 on screw 24 provides separation between the upper portions of cover plates 20, 22 when screw 24 is tightened.

Aligned notches 21, 23 are provided in the lower portions of side plates 20, 22 between drive gear 32 and the ends of the plates. The notches open through the lower ends of the plates and extend in an upward direction to a point just below the teeth of the drive gear. The lower end portions of the side plates thus have a fork-like configuration which is adapted to engage a driven element such as the jack screw of the bone separator from the side, with the screw being rotatively received in the notches and the teeth of gear 32 in tangential driving engagement with the driven element.

Figure 3:
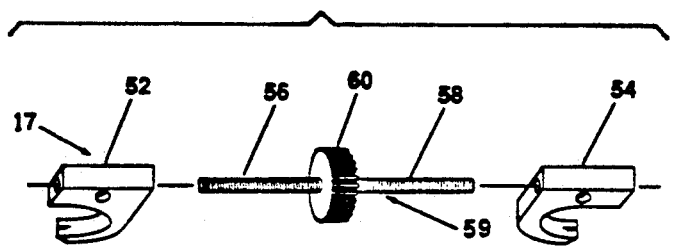
FIG. 3 is an exploded view of the bone separator in the embodiment of FIG. 1.

As illustrated in FIG. 3, the bone separator has a pair of jaws in the form of oppositely facing semicircular hooks 52, 54 threadedly mounted on oppositely threaded sections 56, 58 of a jack screw 59 for movement toward and away from each other upon rotation of the screw. In this particular embodiment, screw section 56 has a left hand thread and section 58 has a right hand thread. A drive gear 60 is affixed to the screw between the two threaded sections and adapted for driving engagement by the drive gear 32 of the driving tool. A suitable gear for meshing engagement with a drive gear having the specifications given above is an 18 tooth spur gear having a diameter of 0.5 inch and a thickness or width of 0.16 inch.

Figure 4:
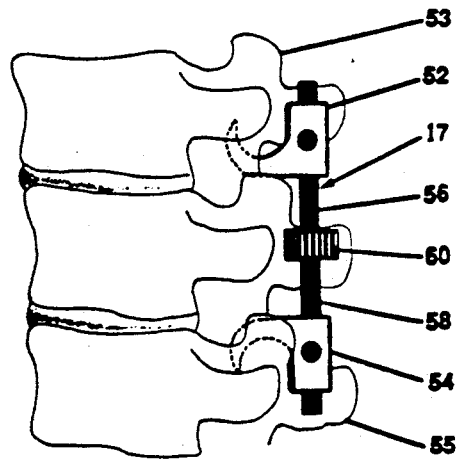
FIG. 4 is an elevational view illustrating the bone separator in the embodiment of FIG. 1 in connection with the spinal bones.

Operation and use of the driving tool in the installation of a spinal bone separator, e.g. during spinal fusion surgery, is as follows. Hooks 52, 54 are initially positioned close together on jack screw 59 and hooked between the two spinal bones 53, 55 to be separated, as illustrated in FIG. 4. The driving tool is then brought into engagement with the jack screw, with pawl spring 40 facing away from the direction the screw is to be rotated to separate the hooks. The fork-like end portions of side plates 20, 22 fit over the screw from the side so that the screw is rotatively received in notches 21, 23 and the teeth of drive gear 32 are held securely in meshing engagement with the teeth of gear 60 for tangentially driving the same.

With the drive gears engaged, the tool can be swung back and forth about the axis of the screw and will drive the screw with a ratcheting action. When the tool is swung away from the direction the pawl spring faces, the end of the spring engages the teeth of drive gear 32, preventing that gear from turning, which causes the driving force of the tool to be transmitted tangentially to the drive gear 60 on the screw. When the tool is swung in the direction the pawl spring faces, drive gear 32 turns freely, and no force is transmitted to the screw. Thus, a back and forth movement of the tool drives the screw in a given direction with the tool in continuous engagement with the screw.

The direction in which the screw is rotated can be reversed by disengaging the driving tool from the screw, rotating the tool 180° about its longitudinal axis so the pawl spring faces in the opposite direction, and reengaging the tool with the screw. Thus, the tool can be used to turn the screw in the bone separating device to either increase or decrease the separation of the bones.

In spinal fusion surgery, the bones to be separated are located deep in the back where space and visibility are both quite limited. These conditions make the installation and adjustment of a bone separator quite difficult, and the problem is further complicated by the fact that the access to the ends of the screw which operates the separator is obstructed by the jaws or hooks of the device and by nearby bones and tissue. Even under these conditions, driving tool 16 can be engaged relatively easily with the operating screw of the bone separator. The tool can turn the screw in a mimimum of space since it only requires enough movement to advance the drive gear one step of the ratcheting mechanism at a time. With a handle having a length on the order of five inches, a back and forth movement of an inch or two at the outer end of the handle is generally sufficient.

Once engaged, the tool remains in continuous engagement with the screw until the adjustment is completed. This greatly simplifies the task of the doctor in installing the separator during surgery.

Figure 5:
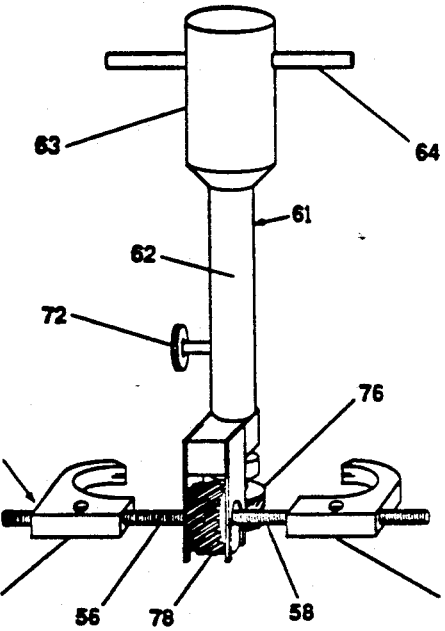
FIG. 5 is an isometric view of another embodiment of a continuously engaged torquing tool according to the invention in driving engagement with a bone separator of the type employed in spinal fusion surgery.
Figure 6:
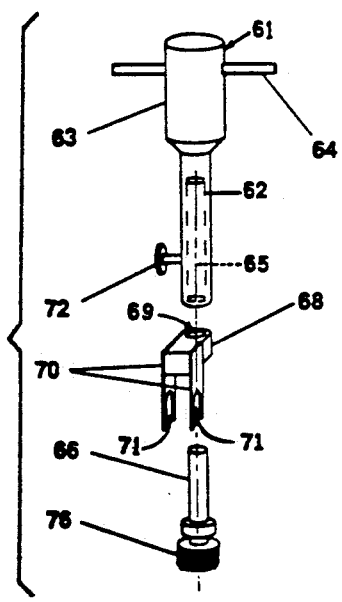
FIG. 6 is an exploded view of the torquing tool in the embodiment of FIG. 5.
Figure 7:
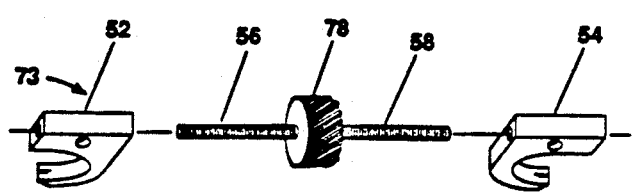
FIG. 7 is an exploded view of the bone separator in the embodiment of FIG. 5.

FIGS. 5-7 illustrate an embodiment of the tool which is particularly suitable for use in situations where space is so limited that it might not be possible to swing a handle back and forth a sufficient distance to actuate a ratchet.

In this embodiment, the tool 61 has an elongated handle 62 with an enlarged upper portion 63, and a crossbar 64 extending laterally from the upper portion. A drive gear 76 is affixed to a shaft 66 which is received in an axial bore 65 in the lower portion of the handle, with a setscrew 72 securing the shaft to the handle. Drive gear 76 is a helical gear of suitable pitch and diameter, and in one suitable embodiment it has a pitch diameter of 0.33 inch.

A generally rectangular block 68 having a vertically extending bore 69 of slightly greater diameter than shaft 66 is rotatively mounted on the shaft between drive gear 76 and the lower end of handle 62, with the shaft passing through the bore in the block. Side plates 70 are affixed to opposite sides of the block, with a pair of aligned notches 71 opening through the lower ends of the plates to form a fork-like structure for engaging a driven element to hold drive gear 76 in tangential driving engagement with that element.

The bone separator 73 which is illustrated in FIGS. 5-7 is similar to the separator 17 illustrated in FIGS. 1-4, and like reference numerals designate corresponding elements in the two embodiments. In separator 73, however, drive gear 78 is a helical gear which is adapted for driving engagement by the helical drive gear 76 of tool 61.

Operation and use of the driving tool 61 with the bone separator 73 is as follows. The jaws or hooks of the separator are positioned between the bones to be separated, as in the previous embodiment. The tool is brought into driving engagement with the separator screw by moving the tool toward the screw until the screw is received in the notches 71 in the fork-like side plates 70, and the drive gear 76 is in meshing engagement with gear 78. With the gears meshed, handle 62 is rotated about its axis to turn drive gear 76 and thus turn the separator screw about its axis to move the separator jaws or hooks. The handle can be turned in either direction, depending upon the direction in which the jaws or hooks are to be moved.

The rotary driving tool 61 of FIGS. 5-7 can be utilized in many of the same applications as the ratcheting tool 16 of FIGS. 1-4, and it can also be utilized in applications where there might not be enough room to swing the handle of the ratcheting tool.

In spinal fusion surgery, driving tool 61 can be easily engaged with the adjusting screw of the bone separator even though space and visibility may both be severely limited. The tool can be used where space is minimal since the handle 62 extends completely out of the surgical work area and can be easily rotated without hitting any bones or tissue. Like the embodiment of FIGS. 1-4, the tool remains in continuous engagement with the driven element and greatly simplifies the task of the doctor in installing bone separating devices during back fusion surgery even though space is limited and the ends of the screw are inaccessable because of the hooks or jaws of the device as well as nearby bones and tissue.

Figure 8:
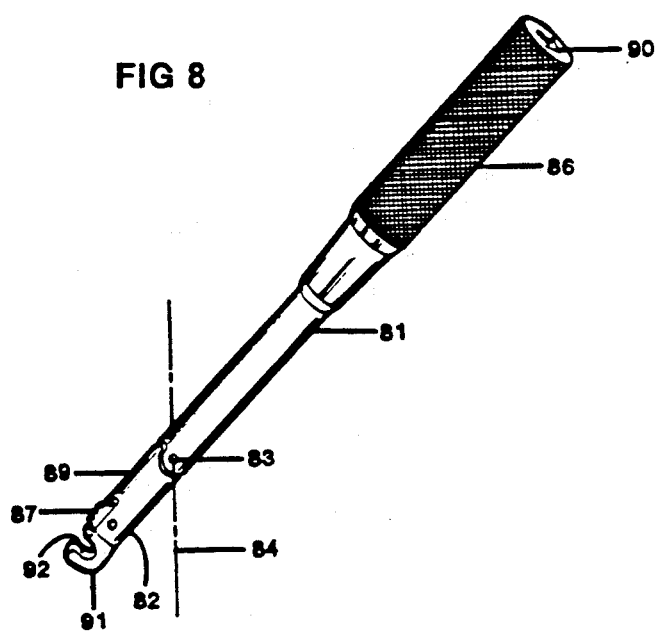
FIG. 8 is an isometric view of another embodiment of a continuously engaged torquing tool according to the invention.

The embodiment of the tool illustrated in FIG. 8 has an articulating handle 81, which enables the tool to turn a driven element through a greater angle of rotation in certain applications than a tool with a rigid handle. The tool has a relatively short head 82 to which the handle is connected by a pin 83 for movement about an axis 84 parallel to the axis of the driven element. The outer portion of the handle has a knurled section 86 to facilitate gripping.

A drive gear 87 is rotatively mounted in the head of the tool for rotation about an axis parallel to pivot axis 84 and the axis of the driven element. A pawl spring 89 engages the teeth of the drive gear and permits it to rotate in one direction only. An arrow 90 is engraved or stamped on the upper end of handle 81 to indicate the direction of handle rotation in which the pawl spring provides a positive driving connection between the head and the drive gear. The distal end of the head is bifurcated and has a pair of hook-like fingers or jaws 91 with laterally facing openings 92 for receiving the shaft of the driven element and holding drive gear 87 in tangential driving engagement with the driven element. This tool can be used for adjusting bone separators of the type shown in FIGS. 1-4, as well as in other applications where continuous engagement and tangential drive are desired.

With the articulating handle, the tool is particularly suitable for use where space limitations would prevent a tool with a rigid handle from providing more than a few degrees of rotation. This is possible because the relatively short head 82 can rotate through a greater angle in a given lateral space than a longer, rigid handle. Thus, the articulating tool is particularly useful in spinal fusion surgery where space is quite limited.

Figure 9A:
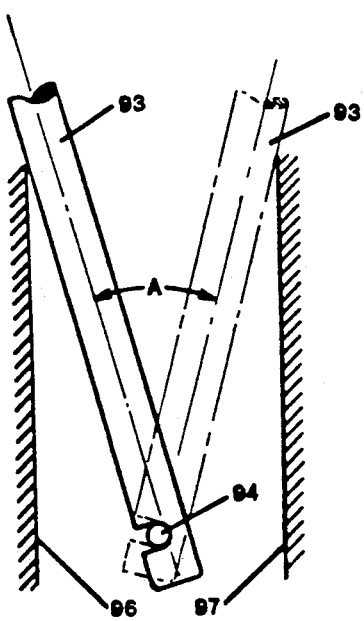
FIG. 9a and 9b are operational views illustrating the use of the embodiment of FIG. 8.
Figure 9B:
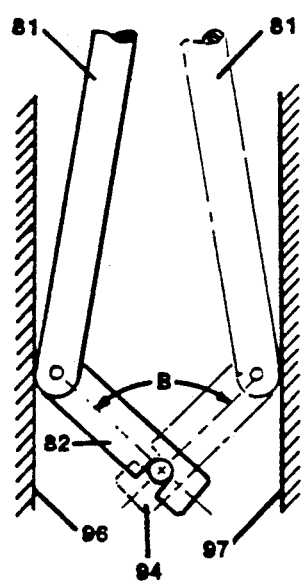

The additional rotation provided by the articulating handle is illustrated in FIGS. 9a and 9b. In these figures, the articulating tool 81 and a rigid tool 93 are each shown in use with a driven element 94 in a relatively narrow space bounded on the sides by walls 96, 97. With the rigid tool, angle of rotation is limited by contact between the handle and the side walls, and the driven element is turned through an angle A of only a few degrees of rotation as the handle moves from wall 96 to wall 97. With the articulating tool, the limiting factor is the contact between the relatively short head 82 and the side walls, and the head travels through an angle B which is substantially greater than the angle travelled by the longer handle in moving from wall to wall. In applications where the distance between the walls is greater than the length of the head, the head can rotate through an angle of 90°-180°, or more, while a rigid handle could move only a few degrees.

While the invention has been described with specific reference to several embodiments of tools for driving the operating screws of bone separators which are utilized in spinal fusion surgery, it is not limited to such applications, and can be employed in other applications where a tangential drive and continuous engagement between the driving tool and the driven element are desired. It is likewise not limited to a particular type of drive gear such as a spur gear or a helical gear. Other types of gears can be employed, as can other types of tangential driving elements such as friction wheels and notched wheels.

Different techniques can be used to provide the tangential drive force in place of the back and forth ratcheting action or the rotational action of the embodiments described. If desired, the drive gear can be replaced with other elements such as springs or push/pull devices to provide a tangential driving force directly to the driven element. Elements having different diameters can be used for the driving element and the driven element to change the mechanical advantage of the drive.

The invention has a number of important features and advantages. It provides a simple and effective tool that is capable of continuously turning a driven element without disengaging the tool even though both ends of the driven device are obstructed or otherwise inaccessible. The tool can be utilized in applications where space for manipulating a tool is severely limited as, for example, in spinal fusion surgery or in complex mechanical or electrical assemblies. The tool is easy to position on the driven device even when visual observation of the device is partially blocked. The tool requires a minimum of lateral clearance space in order to function, and it can be manufactured economically without complex production techniques.

It is apparent from the foregoing that a new and improved tool has been provided for driving elements which cannot be engaged from their ends. While only certain presently preferred embodiments have been described in detail, as will be apparent to those familiar with the art, certain changes and modifications can be made without departing from the scope of the invention as defined by the following claims.

I claim:

1. A continuous drive torquing apparatus for rotating a driven element about its axis, comprising a peripheral driving element adapted t be moved in a radial direction into and out of peripheral driving engagement with the driven element, a head which carries the driving element and is adapted to impart a driving torque to the driving element when swung back and forth about the axis of the driven element with the driving element in peripheral driving engagement with the driven element, an elongated handle for swinging the head back and forth about the axis of the driven element, and means pivotally connecting the elongated handle to the head for movement about an axis parallel to the axis of the driven element to permit articulation between the handle and the head as the head is swung back and forth to produce the tangential driving force with the driving element in peripheral driving engagement with the driven element.

2. The apparatus of claim 1 wherein the driving element comprises a rotatively driven gear having peripheral teeth for engagement with the driven element.

3. The apparatus of claim 1 wherein the head includes a pair of aligned notches for rotatively receiving a portion of the driven element and positioning the driving element a predetermined distance from the axis of the driven element with the driving element in peripheral driving engagement with the driven element.

4. The apparatus of claim 1 wherein the head includes a ratchet which provides a driving connection with the driving element when the head is moved in one direction and permits the head to move freely in another direction without connection to the driving element.

5. In combination: an axially extending drive screw having a pair of oppositely threaded portions and a peripherally engagable drive portion between the threaded portions, a pair of elements threadedly mounted on the threaded portions for movement toward or away from each other upon rotation of the screw, a wrench head, a driving element carried by the wrench head and adapted to be engaged from the side with the drive portion of the screw, means operatively connecting the wrench head to the driving element in such manner that back and forth movement of the head about the axis of the driven element produces a tangential driving force at the driving element, means for holding the driving element in peripheral driving engagement with the drive portion of the screw so that the tangential driving force produced by movement of the wrench head is applied to the drive portion to rotate the screw, an elongated handle for moving the wrench head back and forth about the axis of the driven element, and means pivotally connecting the elongated handle to the wrench head for movement about an axis parallel to the axis of the drive screw to permit articulation between the handle and the wrench head as the wrench head is moved back and forth to produce the tangential driving force.

6. The apparatus of claim 5 wherein the driving element and the drive portion of the screw are gears having teeth which mesh with each other when the driving element is in driving engagement with the drive portion.

7. The apparatus of claim 5 wherein the means for holding the driving element in peripheral driving engagement with the driving portion of the screw comprises a pair of aligned notches for rotatively receiving portions of the screw on opposite sides of the driving portion and positioning the driving element a predetermined distance from the axis of the screw.

8. The apparatus of claim 5 wherein the means operatively connecting the wrench head to the driving element comprises a ratchet which provides a driving connection with the driving element when the head is moved in one direction and permits the head to move freely in another direction without connection to the driving element.

9. A wrench for rotating a driven element about its axis, comprising a head, a drive gear rotatively mounted to the head and adapted for movement in a radial direction into and out of peripheral driving engagement with the rotatable element, ratchet means providing a driving connection between the head and the drive gear when the head is rotated in one direction about the axis of the driven element and permitting the head to rotate freely in the other direction with no driving connection with the gear, means for holding the drive gear in peripheral driving engagement with the driven element so the drive gear imparts a tangential driving force to the rotatable element when the head is rotated in the one direction, an elongated handle for rotating the head back and forth about the axis of the driven element, and means pivotally connecting the elongated handle to the head for movement about an axis parallel to the axis of the driven element to permit articulation between the handle and the head as the head is rotated back and forth to produce the tangential driving force with the driving element in peripheral driving engagement with the rotatable element.

10. The wrench of claim 9 wherein the means for holding the drive gear in peripheral driving engagement with the rotatable element comprises fork means having a pair of aligned notches for rotatively receiving a portion of the rotatable element and holding the drive gear a predetermined distance from the axis of the driven element.

* * * * *